United States Patent [19]

Hokama

[11] 3,941,580

[45] Mar. 2, 1976

[54] HERBICIDAL COMPOSITIONS
[75] Inventor: Takeo Hokama, Chicago, Ill.
[73] Assignee: Velsicol Chemical Corporation, Chicago, Ill.
[22] Filed: Jan. 8, 1975
[21] Appl. No.: 539,371

Related U.S. Application Data
[62] Division of Ser. No. 383,932, July 30, 1973, Pat. No. 3,890,373.

[52] U.S. Cl. ............................................... 71/107
[51] Int. Cl.² .......................................... A01N 9/20
[58] Field of Search ..................................... 71/107

[56] References Cited
UNITED STATES PATENTS
3,736,112   5/1973   Abramitis et al. .................... 71/110

Primary Examiner—Lewis Gotts
Assistant Examiner—Catherine L. Mills
Attorney, Agent, or Firm—Robert J. Schwarz; Dietmar H. Olesch

[57] ABSTRACT

This invention discloses compounds of the formula

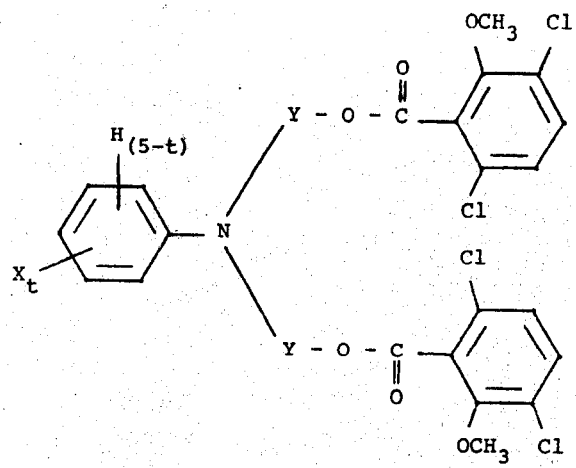

wherein X is alkyl; $t$ is an integer from 0 to 3; Y is a straight or branched alkylene chain of from 2 to 3 carbon atoms. The compounds of the above description are useful as herbicides which resist leaching in the soil.

4 Claims, No Drawings

HERBICIDAL COMPOSITIONS

This is a division of my copending application Ser. No. 383,932, filed July 30, 1973 now U.S. Pat. No. 3,890,373, issued June 17, 1973.

This invention relates to new compositions of matter and more specifically relates to new chemical compounds of the formula (I)

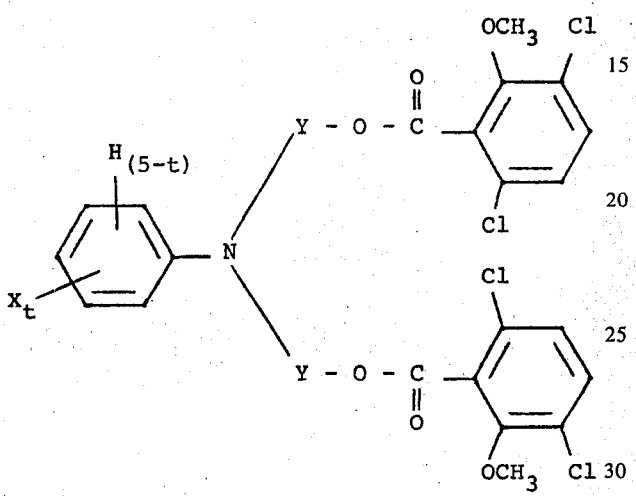

wherein X is alkyl; $t$ is an integer from 0 to 3; Y is a straight or branched alkylene chain of from 2 to 3 carbon atoms. The compounds of the above description are useful as herbicides which resist leaching in the soil.

In a preferred embodiment of the present invention X is lower alkyl having a straight or branched carbon chain of up to about 6 carbon atoms.

The compounds of the present invention are useful as herbicides and possess the unexpected property of resisting leaching in the soil. Weeds often grow near the soil surface whereas many beneficial plants have their roots deeper in the ground. Thus, to avoid injury to the beneficial plants which may be partially sensitive to a herbicide, it is desirable to minimize leaching or downward movement of the herbicide in the soil. Furthermore, a basis for the pre-emergence action of herbicides is often the difference in depth between the planted crop seeds and the weed seeds on the surface of the soil. Crop seeds are generally planted one to three inches deep and are somewhat protected from chemicals applied to the soil surface, while weed seeds generally germinate only in the top one-fourth inch of the soil and are thus subject to much higher concentration of the chemical. To maintain this difference in concentration of the chemical it is desirable to have a herbicide which is resistant to leaching in the soil. The compounds of the present invention resist leaching to a high degree.

The compounds of the present invention can be readily prepared by reacting a molar amount of a compound of the formula (II)

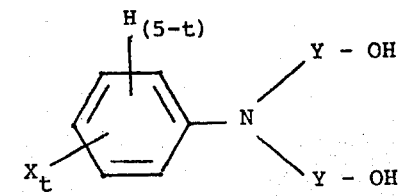

wherein X, $t$ and Y are as heretofore described, with two molar amounts of 2-methoxy-3,6-dichlorobenzoyl chloride. This reaction can be effected by combining the reactants in an inert organic solvent, such as benzene, in the presence of an acid acceptor such as a tertiary amine. The reaction mixture can then be heated at its reflux temperature for a period of from about 2 to about 12 hours. After this time the mixture can be washed with water, with dilute aqueous acid and with aqueous base to remove unreacted starting materials. The mixture can then be washed again with water and dried over anhydrous magnesium sulfate. The dried mixture is then stripped of solvent under reduced pressure to yield the desired product as the residue.

The compounds of formula II when not readily available can be conveniently prepared from the corresponding aniline by reaction with ethylene oxide or propylene oxide.

The manner in which the compounds of the present invention can be prepared is more specifically illustrated in the following examples.

EXAMPLE 1

Preparation of N,N-Bis(2-methoxy-3,6-dichlorobenzoyloxyethyl)aniline

N-Phenyl-N,N-diethanolamine (18.1 grams; 0.1 mole), 2-methoxy-3,6-dichlorobenzoyl chloride (47.3 grams; 0.2 mole), pyridine 16 grams; 0.2 mole) and benzene 150 ml) were charged into a glass reaction vessel equipped with a mechanical stirrer, thermometer and reflux condenser. The mixture was heated at reflux, with stirring for a period of about 5 hours. After this time the reaction mixture was washed with water, extracted with dilute aqueous hydrochloric acid and washed with 5% aqueous sodium carbonate and water. The washed mixture was then dried over anhydrous magnesium sulfate. The dried mixture was then stripped of solvent under reduced pressure to yield the desired product N,N-bis(2-methoxy-3,6-dichlorobenzoyloxyethyl)aniline as a red gum.

EXAMPLE 2

Preparation of N,N-Bis(2-methoxy-3,6-dichlorobenzoyloxypropyl)aniline

N-Phenyl-N,N-dipropanolamine (21 grams; 0.1 mole), 2-methoxy-3,6-dichlorobenzoyl chloride (47.3 grams; 0.2 mole), pyridine (16 grams; 0.2 mole) and benzene (150 ml) are charged into a glass reaction vessel equipped with a mechanical stirrer, thermometer and reflux condenser. The mixture is heated at reflux, with stirring, for a period of about 6 hours. After this time the mixture is washed with water and is dried over anhydrous magnesium sulfate. The dried mixture is then stripped of solvent under reduced pressure to yield the desired product N,N-bis(2-methoxy-3,6-dichlorobenzoyloxypropyl)aniline as the residue.

EXAMPLE 3

Preparation of
N,N-Bis(2-methoxy-3,6-dichlorobenzoyloxyethyl)-4-methylaniline

N-(4-Methylphenyl)-N,N-diethanolamine (19.5 grams; 0.1 mole), 2-methoxy-3,6-dichlorobenzoyl chloride (47.3 grams; 0.2 mole), pyridine (16 grams; 0.2 mole) and benzene (150 ml) are charged into a glass reaction vessel equipped with a mechanical stirrer, reflux condenser and thermometer. The reaction mixture is heated at reflux for a period of about 5 hours. After this time the mixture is washed with water and is dried over anhydrous magnesium sulfate. The dried mixture is then stripped of solvent under reduced pressure to yield the desired product N,N-bis(2-methoxy-3,6-dichlorobenzoyloxyethyl)-4-methylaniline as the residue.

Additional compounds within the scope of the present invention can be prepared by the methods described in the foregoing examples. In the following examples are given the essential starting materials required to prepare the indicated named compounds by the procedure heretofore described.

EXAMPLE 4

N-(3-Propylphenyl)-N,N-diethanolamine + 2-methoxy-3,6-dichlorobenzoyl chloride = N,N-bis(2-methoxy-3,6-dichlorobenzoyloxyethyl)-3-propylaniline.

EXAMPLE 5

N-(4-Hexylphenyl)-N,N-diethanolamine + 2-methoxy-3,6-dichlorobenzoyl chloride = N,N-bis(2-methoxy-3,6-dichlorobenzoyloxyethyl)-4-hexylaniline.

EXAMPLE 6

N-(3,4-Dimethylphenyl)-N,N-diethanolamine + 2-methoxy-3,6-dichlorobenzoyl chloride = N,N-bis(2-methoxy-3,6-dichlorobenzoyloxyethyl)-3,4-dimethylaniline.

EXAMPLE 7

N-(2,4,5-Trimethylphenyl)-N,N-diethanolamine + 2-methoxy-3,6-dichlorobenzoyl chloride = N,N-bis(2-methoxy-3,6-dichlorobenzoyloxyethyl)-2,4,5-trimethylaniline.

Additional compounds within the scope of the present invention are N,N-bis(2-methoxy-3,6-dichlorobenzoyloxyethyl)-3-ethylaniline, N,N-bis(2-methoxy-3,6-dichlorobenzoyloxyethyl)-4-butylaniline, N,N-bis(2-methoxy-3,6-dichlorobenzoyloxyethyl)-4-pentylaniline, N,N-bis(2-methoxy-3,6-dichlorobenzoyloxyethyl)-3,4-diethylaniline, N,N-bis(2-methoxy-3,6-dichlorobenzoyloxyethyl)-3,4-diethylaniline, N,N-bis(2-methoxy-3,6-dichlorobenzoyloxyethyl)-3,4-dipropylaniline, N,N-bis(2-methoxy-3,6-dichlorobenzoyloxyethyl)-2,4-dihexylaniline, N,N-bis(2-methoxy-3,6-dichlorobenzoyloxyprop-2-yl)-4-methylaniline, N,N-bis[2-(2-methoxy-3,6-dichlorobenzoyloxy)propyl]-2-ethylaniline, N,N-bis(2-methoxy-3,6-dichlorobenzoyloxypropyl)-3-propylaniline, N,N-bis(2-methoxy-3,6-dichlorobenzoyloxypropyl)-4-butylaniline, N,N-bis(2-methoxy-3,6-dichlorobenzoyloxypropyl)-4-pentylaniline, N,N-bis(2-methoxy-3,6-dichlorobenzoyloxypropyl)-3,4-dimethylaniline, N,N-bis(2-methoxy-3,6-dichlorobenzoyloxypropyl)-3,4-diethylaniline, N,N-bis(2-methoxy-3,6-dichlorobenzoyloxypropyl)-3,4-dihexylaniline, N,N-bis(2-methoxy-3,6-dichlorobenzoyloxypropyl)-3,4,5-trimethylaniline, N,N-bis(2-methoxy-3,6-dichlorobenzoyloxypropyl)-3,4,5-triethylaniline and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 8

Preparation of a Dust
Product of Example 1   10
Powdered Talc   90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the compound N,N-bis(2-methoxy-3,6-dichlorobenzoyloxyethyl)aniline formulated as aqueous emulsions of acetone solution containing emulsifiers was sprayed at the indicated concentrations on the surface of the soil.

After spraying, the soil containers were placed in the greenhouse and provided with supplementary heat as required and daily or more frequent watering. The plants were maintained under these conditions for a period of 28 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Weed Species | Injury Rating Rate in lbs./acre | | |
|---|---|---|---|
| | 4 | 1 | 0.25 |
| Yellow Nutsedge | 9 | 5 | 0 |
| Wild Oats | 9 | 5 | 0 |
| Jimsonweed | 10 | 9 | 5 |
| Velvetleaf | 10 | 9 | 5 |
| Johnsongrass | 9 | 7 | 0 |
| Pigweed | 10 | 10 | 9 |
| Mustard | 10 | 10 | 7 |
| Yellow Foxtail | 9 | 6 | 2 |
| Watergrass | 10 | 7 | 0 |
| Crabgrass | 10 | 8 | 0 |
| Cheatgrass | 9 | 4 | 0 |
| Morningglory | 10 | 10 | 5 |

The resistance to leaching of the compounds of the present invention can be demonstrated in experiments wherein the migration of the compounds of this invention through soil is measured. In these experiments a plastic column is packed with soil which has previously been dried and passed through a 30 mesh screen. The column can be packed to a soil depth of about 9 inches. The test compound is then applied to the soil surface in an amount equivalent to 15 to 20 pounds per acre. Water, in an amount equivalent to 6 inches of rain, is then poured on top of the soil column in a single addition. The column is allowed to stand for a period of 24 hours during which time the water eluted from the bottom of the column is collected. After this time the column is sawed into three 3 inch sections. The water eluant and the soil fractions are then analyzed for the amount of test compound present. This analysis can be carried out by extracting the test compound present in each soil fraction and in the eluant with ethyl ether, saponifying the compound present in the extracts with sodium hydroxide and thereafter hydrolyzing the sodium salt with hydrochloric acid thereby converting the test compound to 2-methoxy-3,6-dichlorobenzoic acid. The acid is then esterified to its methyl ester and the resulting sample is subjected to quantitative gas chromatography. The stoichiometric conversion and subsequent analysis of the test compound in the various soil fractions and in the water eluant demonstrates the resistance to leaching of the compounds of this invention.

I claim:

1. A herbicidal composition comprising an inert carrier and, as an essential active ingredient, in an amount toxic to weeds, a compound of the formula

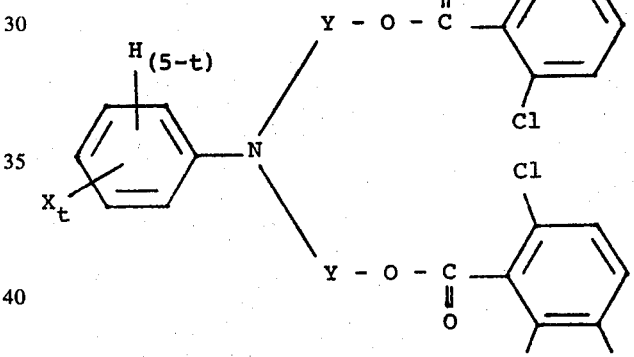

wherein X is lower alkyl; $t$ is an integer from 0 to 3; and Y is a straight or branched alkylene chain of from 2 to 3 carbon atoms.

2. A method of controlling weeds which comprises contacting said weeds with a herbicidal composition of claim 1.

3. The herbicidal composition of claim 1 wherein the essential active ingredient is N,N-bis(2-methoxy-3,6-dichlorobenzoyloxyethyl)aniline.

4. A method of controlling weeds which comprises contacting said weeds with a herbicidal composition of claim 3.

* * * * *